United States Patent
Li et al.

(10) Patent No.: US 9,498,416 B2
(45) Date of Patent: Nov. 22, 2016

(54) ORAL CARE COMPOSITIONS HAVING IMPROVED RHEOLOGY

(71) Applicant: The Procter & Gamble Company, Cincinnati, OH (US)

(72) Inventors: Yujun Li, Beijing (CN); Ross Strand, Beijing (CN); Xin Sun, Beijing (CN); Haiqiu Tang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/635,196

(22) Filed: Mar. 2, 2015

(65) Prior Publication Data
US 2015/0328132 A1    Nov. 19, 2015

(51) Int. Cl.
| | |
|---|---|
| *A61K 8/06* | (2006.01) |
| *A61K 8/02* | (2006.01) |
| *A61K 8/27* | (2006.01) |
| *A61K 8/73* | (2006.01) |
| *A61Q 11/00* | (2006.01) |
| *A61K 8/86* | (2006.01) |
| *A61K 8/365* | (2006.01) |
| *A61K 8/39* | (2006.01) |

(52) U.S. Cl.
CPC .............. *A61K 8/27* (2013.01); *A61K 8/0241* (2013.01); *A61K 8/062* (2013.01); *A61K 8/365* (2013.01); *A61K 8/39* (2013.01); *A61K 8/73* (2013.01); *A61K 8/731* (2013.01); *A61K 8/86* (2013.01); *A61Q 11/00* (2013.01); *A61K 2800/21* (2013.01); *A61K 2800/30* (2013.01); *A61K 2800/48* (2013.01)

(58) Field of Classification Search
USPC .................. 180/311; 424/48, 49, 52; 435/49
See application file for complete search history.

(56) References Cited

U.S. PATENT DOCUMENTS

| | | | |
|---|---|---|---|
| 7,648,363 B2 * | 1/2010 | Oniki ................... | A61K 8/0208 424/49 |
| 2006/0134020 A1 * | 6/2006 | Robinson ............. | A61K 8/0216 424/52 |
| 2008/0230298 A1 * | 9/2008 | Buch ..................... | A61C 5/062 180/311 |
| 2013/0280182 A1 | 10/2013 | Burgess et al. | |
| 2013/0344120 A1 | 12/2013 | Scott et al. | |
| 2014/0314690 A1 * | 10/2014 | Fisher .................... | A61K 8/25 424/49 |

FOREIGN PATENT DOCUMENTS

| | | |
|---|---|---|
| EP | 2 057 978 A1 | 5/2009 |
| WO | WO 2008/005548 A2 | 1/2008 |
| WO | WO 2011/031807 A2 | 3/2011 |
| WO | WO 2011/157497 A1 | 12/2011 |

OTHER PUBLICATIONS

PCT/CN2014/077427 International Search Report and Written Opinion dated Feb. 17, 2016.

* cited by examiner

*Primary Examiner* — Walter Webb
(74) *Attorney, Agent, or Firm* — Alexandra S. Anoff (57) ABSTRACT

Oral care compositions comprising have improved stability due to the removal of stannous ions and the inclusion of low molecular weight polyethylene glycols (PEGs). Compositions containing a source of zinc ions and PEG having a weight average molecular weight of 300 Da to 8000 Da and used for treating the oral cavity comprising administering to the oral cavity an oral care composition according to the present invention.

16 Claims, 2 Drawing Sheets

FIG. 1 – SnCl$_2$ & CMC containing Oral Care Composition

FIG. 2A – 2.3% Polymer without PEG

FIG. 2B – 2.3% Polymer with 1% PEG

ORAL CARE COMPOSITIONS HAVING IMPROVED RHEOLOGY

CROSS REFERENCE TO RELATED APPLICATION

This application claims the benefit of Application No. CN2014/077427 filed May 14, 2014.

FIELD OF THE INVENTION

The present invention relates to oral care compositions having improved stability via the removal of stannous ions and inclusion of low molecular weight polyethylene glycols (PEGs).

BACKGROUND OF THE INVENTION

Traditionally, tin (II) (stannous) ions are added to oral care compositions to deliver multiple benefits such as anti-microbial effects, control of breath malodor, control of dental plaque growth and metabolism, and reduced gingivitis. However, oral care compositions containing stannous ions (e.g., $SnCl_2$), especially in combination with thickening agents such as sodium carboxymethyl cellulose (CMC), can suffer from poor stability. One of the main reasons for the problem is that $Sn^{2+}$ ion interacts with anionic polymer CMC. Further, $Sn^{2+}$ is prone to oxidation causing the oral care composition to exhibit an unacceptably low viscosity. If a formulation routinely decreases in viscosity, such oral care composition can lack phase stability and tends to undergo phase separation over time.

Additionally, oral care compositions, such as a dentifrice, need to balance a number of important health factors such as cleaning, whitening, gum health, and the like with consumer important properties such as pleasant taste and mouth feel. Taste is primarily driven by the type and level of flavor oils included in the formulations. Mouth feel is a result of the rheology and viscosity of the oral care composition.

With taste, for example, consumers like flavors such as peppermint, spearmint, wintergreen, and cinnamon in their oral care compositions. Flavorants are added to the formulation to provide these flavors. These flavorants belong to the class of materials called "volatile oils", which are generally water-insoluble in aqueous systems at the concentrations needed to provide the desired flavor effects or impact. As a result, solubilizing agents are required. Such solubilizing agents may include: (i) solvents such as ethanol or propylene glycol, and (ii) surfactants such as sodium lauryl sulfate. However, there are challenges with using solvents and surfactants. For example, solvents, particularly at high levels, can impart an unpleasant taste (e.g., bitter, chemical taste) or sensation (e.g., burning). Surfactants used at high levels can impart a bitter or soapy taste and also cause tissue irritation and/or oral cavity desquamation.

With mouth feel, consumers like oral care compositions that are not too runny or too thick and will sit on top of the toothbrush bristles. Polymeric thickeners are commonly used to provide the desirable rheology profile for the oral care compositions. Formulary challenges exist that make it difficult to achieve the desirable mouth feel. For example, too little thickener and the oral care composition can feel watery. Alternatively, too much thickener makes the oral care composition feel gritty in the mouth and difficult to dispense.

A particular challenge for formulating oral care composition that contain essentially water-insoluble components, such as flavor oils, is achieving acceptable phase stability and/or sufficient shelf-life for the product without sacrificing taste and mouth feel. Phase instability tends to be an issue for oral care compositions formulated with flavor oils in combination with other oral care actives via use of emulsions, specifically oil-in-water emulsions. There are two key factors that can impact phase stability of the oral care compositions containing emulsions.

One factor is the viscosity of the external phase (i.e., aqueous phase) surrounding the emulsions. In the case of an oil-in-water emulsion, the decreasing viscosity of the external aqueous phase over time can negatively affect the kinetic stability of the emulsion. For example, the flavor oil molecules can diffuse out of the oil droplet phase into the water phase and then fuse into larger oil droplets. The destabilization caused by the combination of oil droplet collisions and coalescence can lead to the formation of one big oil droplet and the emulsion becoming two separate phases. The time-line for the above reaction can be significantly accelerated in oral care composition having decreased viscosity of the aqueous phase. Current solutions focus on increasing levels of thickeners and/or humectants such as PEGs (see U.S. Patent Publication No. 2013/280182; P&G) to the formulation to modify (i.e., increase) the viscosity of the external aqueous phase and slow down movements of the oil droplets. One disadvantage of using higher levels of thickeners and/or humectants is that it can be expensive. Another disadvantage is that the resulting product can possess an undesirable taste and/or mouth feel.

A second factor that can impact phase stability of the oral care composition is the droplet sizes of the emulsions that form. Droplet sizes impact the emulsions' ability to remain kinetically stable over long periods of time. Prior art approaches to control droplet sizes generally focus on controlling processing conditions.

Thus, the need remains for oral care compositions containing flavorants having improved phase stability and/or shelf-life stability over time (i.e., greater than 4 months to 24 months or longer), preferably at ambient conditions. The need also exist for an oral care composition containing flavorants to have physical and chemical stability across a range of manufacturing, handling and storage conditions. It is desirable that the oral care composition, is a dentifrice, and preferably provide pleasant taste and mouth feel experience.

SUMMARY OF THE INVENTION

Applicants have surprisingly discovered that it is possible to overcome the phase stability problem for an oral care composition containing flavorants, preferably a dentifrice, by regulating the oil droplet sizes of the emulsions that form within the oral care composition to a certain average mean particle size range (i.e., less than 100 nm) by removal of stannous ions (e.g., $SnCl_2$) and inclusion of low molecular weight PEGs, preferably at low levels, can be used to achieve these benefits.

In one aspect, the present invention is directed to an oral care composition comprising: a) from 0.01% to 5%, preferably from 0.1% to 2%, of a zinc ion source; b) from 0.01% to 5%, preferably 0.1% to 2%, of a flavor composition; c) from 30% to 75% of a total water content; d) from 0.1% to 3% of a first humectant comprising polyethylene glycols (PEG) having an average molecular weight range of from 300 Da to 8,000 Da; and e) from 0.01% to 5%, preferably from 0.1% to 3%, or 1% to 2.5%, of a thickener system comprising a combination of sodium carboxymethyl cellulose (CMC), hydroxyethyl cellulose (HEC), and carrageenan. In an embodiment, the oral care composition is substantially free of stannous ions. This minimizes cost and complexity to the formulation.

In another aspect, the present invention relates to a method for treating the oral cavity comprising administering to the oral cavity an oral care composition as described herein above.

One aim of the present invention is to provide an oral care composition as described herein above which can exhibit improved stability.

Another aim of the present invention is to provide such an oral care composition as described herein above with robust oil droplet sizes of the emulsions that form within the oral care composition to allow the composition to exhibit sufficient phase stability such that it does not phase separate after 4 months, preferably after 6 months, more preferably after 12 months, or even more preferably after 24 months, at ambient conditions.

A further aim of the present invention is to provide such an oral care composition as described herein above with high levels (i.e., up to 5%) of flavor oils in combination with other oral care actives via use of emulsion without a significant variation in the phase stability of the composition after 4 to 24 months, at ambient conditions.

A yet further aim of the present invention is to provide such an oral care composition as described herein above with relatively more water-insoluble flavor oils such as, for non-limiting example, peppermint and spearmint, without a significant variation in the phase stability of the composition after 4 to 24 months, at ambient conditions.

These and other features of the present invention will become apparent to one skilled in the art upon review of the following detailed description when taken in conjunction with the appended claims.

BRIEF DESCRIPTION OF THE DRAWINGS

While the specification concludes with claims that particularly point out and distinctly claim the invention, it is believed the present invention will be better understood from the following description of the accompanying figures.

FIGS. 2A and 2B are SEM micrographs of oil droplets according to Example 2. SEM images were obtained using a SEM Hitachi S-4800. The SEM was operated at 3 kV, and 15,000× magnification. The micrograph of FIG. 2A shows multi-layered colloidal droplets from an oral care composition containing 2.3% polymer without PEG (i.e., "Comparative Sample 1"). The micrograph of FIG. 2B shows droplets from an oral care composition containing 2.3% polymer with 1% PEG (i.e., "Present Invention Sample 1").

DETAILED DESCRIPTION OF THE INVENTION

Definitions

As used herein, the term "average molecular weight" refers to the average molecular weight as determined using gel permeation chromatography according to the protocol found in *Colloids and Surfaces A. Physico Chemical & Engineering Aspects*, Vol. 162, 2000, pg. 107-121. Unless otherwise specified, all molecular weight values herein refer to the weight average molecular weight and expressed in g/mol.

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

The term "Dielectric Constant" (DEC) as used herein refers to a convenient measure of polarity of a material such as a flavorant. DEC is measured for a material at 25° C. For example, a suitably polar flavorant material has a DEC measured at 25° C. of greater than 2.5.

The term "oral care composition" as used herein means a product that in the ordinary course of usage is retained in the oral cavity for a time sufficient to contact some or all of the dental surfaces and/or oral tissues for purposes of oral activity. In one embodiment, the composition provides a benefit when used in the oral cavity. The oral care composition of the present invention may be in various forms including toothpaste, dentifrice, tooth gel, tooth powders, tablets, rinse, sub gingival gel, foam, mouse, chewing gum, lipstick, sponge, floss, prophy paste, petrolatum gel, or denture product. In one embodiment, the oral composition is in the form of a paste or gel. In another embodiment, the oral composition is in the form of a dentifrice. The oral composition may also be incorporated onto strips or films for direct application or attachment to oral surfaces, or incorporated into floss.

The term "orally acceptable carrier" as used herein means a suitable vehicle or ingredient, which can be used to form and/or apply the present compositions to the oral cavity in a safe and effective manner.

The term "dentifrice" as used herein means paste, gel, powder, tablets, or liquid formulations, unless otherwise specified, that are used to clean the surfaces of the oral cavity.

The terms "phase stable" and "phase stability" are used interchangeably and refer to the oral care composition visually (i.e., to the unaided eye) having no liquid separation from the composition's body over a defined period of time (under ambient conditions). In other words, phase stable oral care compositions of the present invention can resist syneresis. As used herein, the term "stability" is meant to refer to the emulsion component formed from the flavorant in the oral care composition that will not phase separate under storage conditions from 25° C. up to 40° C. to 50° C., freeze-thaw cycles and vibrational forces such as the type typically encountered during shipping.

The terms "shelf-life stable" and "shelf-life stability" are used interchangeably and refer to the oral care composition being deemed consumer acceptable after a defined period of time after its production (under ambient conditions). The test to determine this is by inverting the dispenser containing the oral care composition and holding it vertically for 10 seconds during which oral care composition should not drip out of the dispenser.

The term "substantially free" as used herein refers to no intentional amount of that material is added to the composition or an amount of a material that is less than 1%, 0.5%, 0.25%, 0.1%, 0.05%, 0.01%, or 0.001% of the composition.

The term "teeth" as used herein refers to natural teeth as well as artificial teeth or dental prosthesis.

The term "total water content" as used herein means both free water and water that is bound by other ingredients in the oral care composition.

The term "water-insoluble" as used herein with respect to flavorants refers to flavor oils which has a water solubility of less than about one grams per 100 grams of water at 25° C.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Oral Care Compositions

In one aspect, it is desirable to produce an oral care composition for practical commercial use that has at least greater than 4 months, greater than 6 months, greater than 1 year, greater than 1.5 years, or up to 2 years, or combinations therein between, of shelf-life stability and/or phase stability.

Specifically, the present invention provides an oral care composition comprising:
 a) from 0.01% to 5%, preferably from 0.1% to 2%, of a zinc ion source by weight of the composition;
 b) from 0.01% to 5%, preferably 0.1% to 2%, by weight of the composition of a flavor composition;
 c) from 30% to 75% by weight of the composition of a total water content;
 d) from 0.1% to 3% by weight of the composition of a first humectants comprising polyethylene glycols (PEGs) having an average molecular weight range of from 300 Da to 8,000 Da; and
 e) from 0.01% to 5%, preferably from 0.1% to 3%, or 1% to 2.5%, by weight of the composition of a thickener system comprising a combination of carboxymethyl cellulose (CMC), hydroxyethyl cellulose (HEC), and carrageenan;
 wherein the oral care composition is substantially free of stannous ions.

In an embodiment, the oral care composition is an oil-in-water emulsion having a dispersed phase comprising oil droplets having an average mean particle size of from 1 nm to 100 nm. In another embodiment, the oral care composition is an oil-in-water emulsion having a dispersed phase comprising oil droplets having an average mean particle size of less than 100 nm, less than 90 nm, less than 80 nm, less than 70 nm, less than 60 nm, less than 50 nm, less than 40 nm, less than 30 nm, or less than 10 nm after 14 days at 40° C.

Free of Stannous Ions

Figure 1:
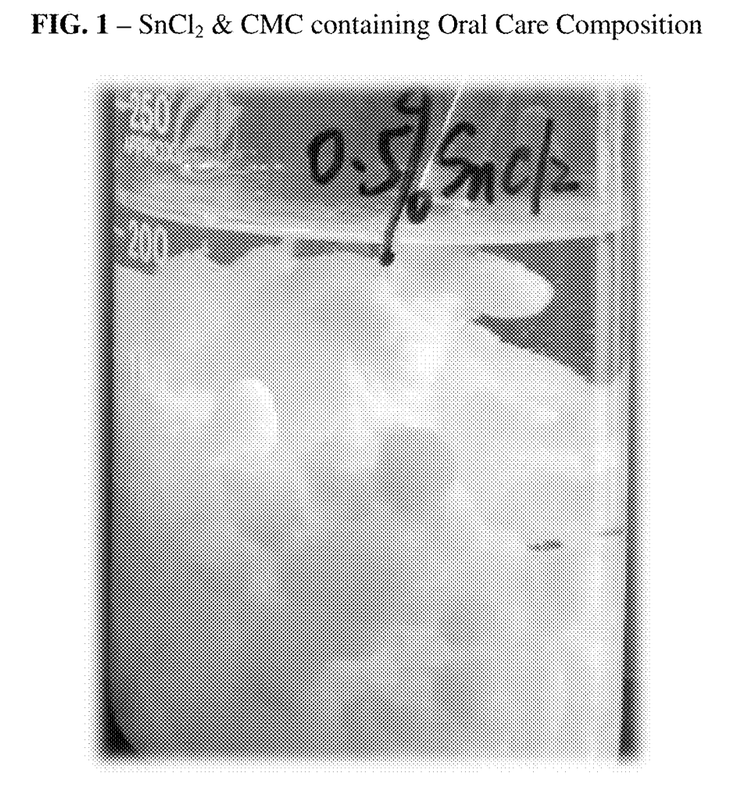
FIG. 1 is a photo of a prior art oral care composition that has undergone phase separation due to the interaction between $SnCl_2$ and CMC.

The present invention is based on the observation that oral care compositions containing stannous ions (e.g., $SnCl_2$) in combination with certain thickening agents, such as charged cellulose derivatives like sodium carboxymethyl cellulose (CMC), suffer from decrease in viscosity of the composition. Over time this leads to the liquid separating from the body of the composition and a phase stability problem (see FIG. 1). Without wishing to be bound by theory, this problem is attributed to the interaction between $SnCl_2$ and CMC, as CMC is an anionic polysaccharide commonly used as a structurant material in oral care compositions. The reaction between oxygen with the unbound Sn ions in the formulation, as follows, makes this interaction even worse:

$$6SnCl_{2\,(aq)} + O_{2\,(g)} + 2H_2O_{(l)} \rightarrow 2SnCl_{4\,(aq)} + 4Sn(OH)Cl_{(s)}$$

Further, it is believed that the higher valent ion (e.g., $Sn^{4+}$) precipitate formed when the stannous oxidization occurs to inhibit the CMC gel hydration. As a consequence, the viscosity of the composition drops and the composition becomes thinner and more watery. Insufficient structuring of the external phase surrounding the emulsions in the oral care composition can speed up the migration of the oil droplets. As a result, larger oil droplets will tend to form faster and the risk for phase separation is accelerated.

Accordingly, Applicants have surprisingly discovered that in order to avoid, or at least mitigate, and to reduce and/or eliminate the phase separation problem oral care compositions should be formulated to be substantially free of stannous ions.

Flavorants

The terms "flavor oils", "flavorants", and "flavor compositions" are used interchangeably and in the broadest sense to include flavor ingredients, or sensates, or sensate agents, or combinations thereof. It is critical for consumer delight to be able to formulate oral care compositions with a wider range of flavorants to include those that are more hydrophobic and less water soluble such as peppermint and spearmint. Further, it is desirable to have the ability to formulate oral care composition with higher than currently practicable levels of flavor oils for flavor impact or extra benefits without having to using higher levels of solvents (e.g., thickeners, humectants). It is also desirable to produce oral care composition having at least 4 months to 24 months shelf-life or phase stability. By stability herein is meant that the emulsion formed from the flavorants and solvents is stable against phase separation under storage conditions up to 40-50° C.

It's particularly challenging to maintain small droplet size formed from the flavorants absent the addition of extra structuring/thickening agents and/or costly or lengthy processing measures. Although flavorants are "volatile oils" and considered water-insoluble, they tend to have some level of water solubility. This slight water solubility makes formulating and stabilization of emulsions containing flavorants difficult. Without wishing to be bound by theory, this is primarily due to the effect called Ostwald Ripening. Ostwald Ripening is the phenomena often found in oil-in-water emulsions in which smaller oil particles in solution spontaneously dissolve and deposit on larger oil particles to reach a more thermodynamically stable state wherein the surface area to volume ratio is minimized. The combination of destabilization by oil droplet collisions and coalescence, in addition to Ostwald Ripening in the case of volatile oils, can lead to the oil phase eventually becoming one big droplet to lower surface energy and minimize total surface area. When this occurs, over time the emulsion becomes unstable and eventually two separate phases. For standard oral care compositions, this may take anywhere from a few weeks to a few months.

In an embodiment, Applicants have solved this formulation challenge by controlling the range of average mean particle size of the oil droplets to be less than 100 nm, less than 90 nm, less than 80 nm, less than 70 nm, less than 60 nm, less than 50 nm, less than 40 nm, less than 30 nm, less than 20 nm, or less than 10 nm. In another embodiment, the oral care composition is an oil-in-water emulsion having a dispersed phase comprising oil droplets having an average mean particle size from 1 nm to 100 nm, from 1 nm to 50 nm, or from 1 nm to 30 nm. In yet another embodiment, the oil droplets have the above prescribed average mean particle size ranges for at least the first week, at least the first two weeks, at least the first three weeks, or at least the first four weeks after production.

Particle size measurements are performed using the Zetasizer Nano which uses a process called Dynamic Light Scattering (DSL). Dynamic Light Scattering (also known as "PCS-Photon Correlation Spectroscopy") measures Brownian motion and relates this to the size of the particle. This is done by illuminating the particle with a laser and analyzing the intensity fluctuations in the scattered light. Details of the method are disclosed in U.S. Patent Publication No. 2013/0344120. The Zeta-sizer Nano System measures the rate of the intensity of the fluctuations and then uses this to calculate the size of the particles using mathematical algorithms.

Peak statistics are calculated using the expressions given below where $Y_i$ is the Y value of the $i^{th}$ Y axis class/bin and $X_i$ is the X axis value in the center of the X axis class/bin. The Y axis here is the Intensity (%) while the X axis is the diameter (nm). Area is defined as the area under each peak, relative to the total area of the distribution. Average mean particle size is defined as the average value of the peak, weighted by the Y axis parameter.

% Area=$\Sigma_i Y_i$

Mean=$pS(_i)I(_i)$/Area

Polydispersity or Width of the Peak=Square root $((\Sigma_{Xi2Yi}/\% \text{ area})-\text{Mean}^2)$ Polydispersity Index ("PDI") is a number calculated from a simple 2 parameter fit to the correlation data (the cummulants analysis). The PDI is dimensionless and scaled such that values smaller than 0.05 are seen with highly monodisperse standards. Values greater than 0.7 indicate that the sample has a very broad size distribution and is probably not suitable for the dynamic light scattering (DLS) technique. The various size distribution algorithms work with data that fall between these two extremes. The calculations for these parameters are defined in the ISO standard document 13321: 1996 E and ISO 22412:2008.

The oral care compositions herein may include from about 0.01% to 5%, alternatively from 0.01% to 4%, alternatively from 0.1% to 3%, alternatively from 0.5% to 2%, alternatively combination thereof, of a flavor composition by weight of the oral care composition. Flavor ingredients may include those described in U.S. Patent Publication No. 2012/0082630A1. Non-limiting examples of flavor compositions or flavor ingredients include: mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, a-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, a-terpineol, linalool, limonene, citral, neral, geranial, geraniol nerol, maltol, ethyl maltol, anethole, dihydroanethole, carvone, menthone, beta-damascenone, ionone, gamma-decalactone, gamma-nonalactone, y-undecalactone, or combinations thereof. Generally suitable flavor ingredients are chemicals with structural features and functional groups that are less prone to redox reactions. These include derivatives of flavor ingredients that are saturated or contain stable aromatic rings or ester groups.

Sensates such as cooling, warming, and tingling agents are useful to deliver signals to the consumer. The most well-known cooling agent is menthol, particularly 1-menthol, which is found naturally in peppermint oil. Among synthetic cooling agents, many are derivatives of or are structurally related to menthol, i.e., containing the cyclohexane moiety, and derivatized with functional groups including carboxamide, ketal, ester, ether and alcohol. Examples include N-(4-cyanomethylphenyl)-ρ-menthanecarboxamide (Evercool 180) and p-menthanecarboxamide compounds such as N-ethyl-p-menthan-3-carboxamide. An example of a synthetic carboxamide cooling agent that is structurally unrelated to menthol is N,2,3-trimethyl-2-isopropylbutanamide. Additional exemplary synthetic cooling agents include alcohol derivatives such as 3-1-menthoxypropane-1,2-diol, isopulegol, p-menthane-3,8-diol; menthone glycerol acetal; menthyl esters such as menthyl acetate, menthyl acetoacetate, menthyl lactate, and monomenthyl succinate.

Non-limiting examples of non-menthol coolants include menthone glycerol acetal (for example, sold as Frescolat® MGA by Haarmann & Reimer), N-(4-cyanomethylphenyl)-ρ-menthanecarboxamide or N-(4-cyanomethylphenyl)-5-methyl-2-(1-methylethyl)cyclohexanecarboxamide (for example, commercially available from Givaudan), N-(2-(pyridin-2-yl)ethyl-3-p-menthanecarboxamide (for example, commercially available from Givaudan), N-(4-sulfamoylphenyl)-ρ-menthanecarboxamide, N-(4-cyanophenyl)-ρ-menthanecarboxamide, N-(4-acetylphenyl)-ρ-menthanecarboxamide, N-(4-hydroxymethylphenyl)-ρ-menthanecarboxamide, N-(3-hydroxy-4-methoxyphenyl)-ρ-menthanecarboxamide, 2-Isopropyl-N,2,3-trimethylbutyramide (for example, known as WS-23); N-Ethyl-ρ-menthane-3-carboxamide (for example, known as WS-3); Ethyl 3-(ρ-menthane-3-carboxamido)acetate (for example, known as WS-5), menthyl lactate (for example, commercially available as Frescolat® ML by Haarmann & Reimer), Menthoxypropane-1,2-diol (for example, commercially available as Coolant Agent 10 by Takasago International), ρ-Menthane-3,8-diol (for example, commercially available as PMD38)—Takasago International, Isopulegol (for example, commercially available under the name "Coolact P®" by Takasago International), (1R,2S,5R)-2-isopropyl-5-methyl-N-(2-(pyridyn-2-yl)ethylcyclohexane carboxamide, (1-glyceryl-p-mentane-3-carboxylate), (ethyleneglycol-p-methane-3-carboxylate), (N-t-butyl-p-menthane-3-carboxamide), (N-(4-,ethoxyphenyl)-p-menthane-3-carboxamide), 3-(1-menthoxy)propane-1,2-diol, 3-(1-Menthoxy)-2-methylpropane-1,2-diol, menthyl pyrrolidone carboxylate) (for example, commercially available as Questice®), (1R,3R,4S)-3-menthyl-3,6-dioxaheptanoate (for example, commercially available from Firmenich), (1R, 2S,5R)-3-menthyl methoxyacetate (for example, commercially available from Firmenich), (1R,2S,5R)-3-menthyl 3,6, 9-trioxadecanoate (for example, commercially available from Firmenich), (1R,2S,5R)-menthyl 11-hydroxy-3,6,9-trioxaundecanoate (for example, commercially available from Firmenich), (1R,2S,5R)-3-menthyl(2-hydroxyethoxy)acetate (for example, commercially available from Firmenich), Cubebol (for example, commercially available from Firmenich), 1-[2-hydroxyphenyl]-4-[2-nitrophenyl-]-1,2,3,6-tetrahydropyrimidine-2-one), 4-methyl-3-(1-pyrrolidinyl)-2 [5H]-furanone (for example, known as Icilin or AG-3-5), menthyl lactate, menthone glycerin acetal, L-Monomenthyl succinate, L-monomenthyl glutarate, 3-1-menthoxypropane-1,2-diol (for example, known as Coolact 10), 2-1-menthoxyethanol (for example, known as Cooltact 5), and mixtures thereof. Additional non-menthol coolants are described in U.S. Pat. No. 7,414,152, U.S. Patent Publication No. US2010/0086498 A1 and PCT Publication No. WO2010/128026 A2. In one embodiment, the non-menthol coolant is N-(4-cyanomethylphenyl)-ρ-menthanecarboxamide including all 8 stereoisomers arising from the 3 chiral centers. In particular, the [1R,2S,5R]—N-(4-cyanomethylphenyl)-ρ-menthanecarboxamide can be readily synthesized from natural 1-menthol.

Additional agents that are structurally unrelated to menthol but have been reported to have a similar physiological cooling effect include alpha-keto enamine derivatives described in U.S. Pat. No. 6,592,884, including 3-methyl-2-(1-pyrrolidinyl)-2-cyclopenten-1-one (3-MPC), 5-methyl-2-(1-pyrrolidinyl)-2-cyclopenten-1-one (5-MPC); 2,5-dimethyl-4-(1-pyrrolidinyl)-3 (2H)-furanone (DMPF); icilin (also known as AG-3-5, chemical name 142-hydroxyphenyl]-4-[2-nitrophenyl]-1,2,3,6-tetrahydropyrimidine-2-one).

Some examples of warming agents include ethanol; nicotinate esters, such as benzyl nicotinate; polyhydric alcohols; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof.

Examples of some tingling agents include capsaicin; homocapsaicin, jambu oleoresin, zanthoxylum peperitum, saanshool-I, saanshool II, sanshoamide, piperine, piperidine, spilanthol, 4-(1-methoxymethyl)-2-phenyl-1,3-dioxolane, or combinations thereof.

Flavorant Polarity

The polarity of flavorant compositions can be characterized by dielectric constant or water index. Individual flavor ingredients, of the flavor composition, can be characterized by its octanol-water partition coefficient.

Measuring the dielectric constant of a flavorant composition is a convenient way to determine the relative polarity of a mixture of flavor ingredients. The Dielectric constant (DEC) is measured by placing a charge across two conductive plates with a test liquid between them. These test materials or dielectrics act as insulators which change the capacitance or charge storage capacity of the circuit. DEC can easily be measured for most liquids by using the Model 870 Dielectric Constant meter produced by Brookhaven. For most liquids used in oral care products the DEC varies from 2 for extremely hydrophobic liquids to 80 for water. Many flavor compositions have DECs from 6 to 11, and individual flavor ingredients can vary from 2 to 22.

In general flavor compositions with the high DEC values solubilize much easier than ones with low values. In general, flavorant compositions are also much easier to emulsify than their individual flavor ingredients (so called "increased mutual solvency"). The DEC of a material is strongly correlated ($R^2$=0.92) to its solubility parameter (SP). SP is a universal parameter used to predict solubility and hydrophobicity of materials. See also "Computation of dielectric constants of solvent mixtures and electrolyte solutions," Wang and Anderko, *Fluid Phase Equilibria* 186, 103 (2001). In one embodiment, a flavorant composition has a DEC from 1 to 3.5 (i.e., "low polarity"), alternatively a DEC from greater than 3.5 to 8 (i.e., "mid-polarity"), or a DEC from greater than 8, alternatively from greater than 8 to 15 (i.e., "high-polarity"). In another embodiment, the flavorant composition has a DEC from 1 to less than 6, alternatively the flavorant composition has a DEC from 6 to 8, alternatively still the flavorant composition has a DEC from 6 to 11.

Water number ("WN") is another test to measure flavor polarity. WN is defined as the grams of water needed to achieve permanent turbidity in a solution comprised of 10 grams flavorant composition and 30 grams of 1,2 hexanediol. In general, WN increases as a function of increasing polarity. WN for most flavor composition vary from around 20 to over 30 grams. In general, values higher than 30 are caused by incorporation of hydrophilic materials such as methyl salicylate, carvone, synthetic Cassia, eugenol, WS 23, MGA, or TK 10. "High Cool Exotic Orange" is an excellent example of a flavorant composition that has a low WN of 7.4 but has a high DEC of 12.6. Without wishing to be bound by theory, the high DEC is due to the presence of coolant agents and the low WN is caused by terpenes. This suggests that this flavorant composition will be more difficult to solubilize than "Cinnamint" that has a WN of 29.7 and a DEC of 12.3.

In one embodiment, a flavorant composition has a WN from 1 to 79, from 1 to 50, or from 1 to 25. In another embodiment, a flavorant composition has a WN below 23 (i.e., "low polarity"), alternatively a WN from 1 to 23, or from 1 to 20, or from 1 to 17, or from 1 to 16, or from 1 to 15, or from 1 to 15, or from 15 and below. In another embodiment, the WN is from 23 to 35 (i.e., "mid-polarity"), alternatively a WN from 23 to 40, or from 23 to 30, or from 23 to 29. In yet another embodiment, the WN is greater than 45 (i.e., "high-polarity"), alternatively the WN is greater than 50, or 55, or 60, alternatively the WN is from 45 to 79. In another embodiment, the flavorant composition has a WN less than 30, alternatively less than 29, or 28, 27, 26, 25, 24, 23, 22, 21, or 21, or at least 1, or 2, 3, alternatively from 1 to 30, and combination thereof.

The individual flavor ingredients (that comprise a flavorant composition) of the present invention may be defined by their octanol/water partition coefficient ("P"). The octanol/water partition coefficient of a flavor ingredient is the ratio between its equilibrium concentrations in octanol and in water. The partition coefficients of flavorant ingredients may more conveniently be given in the form of its logarithm to the base 10, log P. The log P values of many flavorant ingredients have been reported. See, e.g., the Pomona 92 database, available from Daylight Chemical Information Systems, Inc. ("Daylight CIS"), Irvine, Calif. However, the log P values are most conveniently calculated by the Biobyte C log P program contained in Daylight Software version 4.94, also available for license from Daylight CIS. This program also lists experimental log P values when they are available in the Pomona92 database.

The calculated log P ("C log P") is determined by the fragment approach of Hansch and Leo (cf, A. Leo, in Comprehensive Medicinal Chemistry, vol. 4, C. Hansch, P.

G. Sammens, J. B. Taylor and C. A. Ramsden, Eds., p. 295, Pergamon Press, 1990). The fragment approach is based on the chemical structure of each flavorant ingredient, and takes into account the numbers and types of atoms, the atom connectivity, and chemical bonding. The C log P values, which are the most reliable and widely used estimates for this physicochemical property, are preferably used instead of the experimental log P values in the selection of flavorant ingredients to comprise a flavorant composition.

The C log P values may be defined by the amount of weight percentage of flavorant ingredients below 2.77 C log P. Generally, the greater amount of flavorant ingredients below 2.77 C log P, generally lower the polarity and thus more difficult to solubilize. In one embodiment, the flavorant composition comprises at least 10% by weight of the flavorant composition of one or more flavor components having a Calculated Logarithm of base 10 of octanol/water Partition coefficient (C log P) of less than 2.77, or at least 20 wt %, or at least 30 wt %, or at least 40 wt % of the flavorant components having C log P less than 2.77.

Humectants

The oral care composition comprises from 0.1% to 3% of a first humectant comprising of polyethylene glycols (PEGs) having an average molecular weight range of from 300 Da to 8,000 Da. In an embodiment, the oral care composition comprises from 0.5% to 2%, or 0.75% to 1.5% of a first humectants. In another embodiment, the PEGs have an average molecular weight range of from 300 Da to 1,000 Da, 300 Da to 800 Da, or 300 Da to 600 Da. Such low molecular weight PEGs are commercially available from such suppliers as Dow Chemical and BASF (New Jersey, USA).

Applicants have surprisingly discovered that adding low molecular weight PEGs, as described above, it is possible to increase the flavorants' solubility and efficiently reduce oil droplet sizes of the emulsions to ensure sufficient phase stability and/or shelf-life for the oral care composition. Without wishing to be bound by theory, Applicants believe that low molecular weight PEGs, as co-surfactants, can join and modify emulsion packing pattern between flavorants and surfactants to increase the flavorants solubility and reduce the resulting droplet sizes. Alternatively, low molecular weight PEGs may likely strike an oil droplets.

The oral care composition may further comprising from 35% to 60%, from 40% to 55%, or from 40% to 50%, or combinations thereof, of at least one secondary humectant selected from the group consisting of sorbitol, glycerin, xylitol, butylenes glycol, propylene glycol, trimethyl glycine, and mixtures thereof. In an embodiment, the secondary humectants comprises from 40% to 55% by weight of the oral care composition of sorbitol.

Thickening Agents

The oral care compositions herein may include one or more thickening agents or binders to provide a number of benefits such as, for example, a desirable consistency of the oral care composition, desirable active release characteristics upon use, acceptable shelf-life stability (greater than 4 months to 24 months, or longer), acceptable phase stability (greater than 4 months to 24 months, or longer), and/or suitable viscosity of the oral care composition to reduce and/or prevent acceleration of the oil droplets contained therein. Thickening agents and binders together can form a thickener system.

Thickener system present in the oral care composition is in the range from about 0.01% to about 5%, from 0.1% to 3%, or from 1.0% to 2.5%, and comprises a combination of carboxymethyl cellulose (CMC), hydroxyethyl cellulose (HEC), and carrageenan. In an embodiment, the CMC is sodium carboxymethyl cellulose. For instance, one commercially available form of CMC is CMC 2000S available from CPKelco. In another embodiment, the carrageenan may be selected from the group consisting of Kappa-carrageenan, Iota-carrageenan, Lambda-carrageenan, and combinations thereof. In another embodiment, the HEC has an average molecular weight range of 90,000 g/mol to 1,300,000 g/mol and an average degree of polymerization from 300 to 4,800.

Although increasing thickening agent is one way to improve physical stability, it is not preferred as this approach may slow down the surfactant dispersion and foaming rate, and flavor release rate.

pH

The pH of the oral care composition may be between 4 to 11, from 5 to 10, or 6 to 8. Alternatively, the pH can be greater than 6, alternatively greater than 7, alternatively from 8 to 10, or combinations thereof. The pH is typically measured using a ratio of 1:3 of paste:water, whereby 1 gram of the oral care composition (e.g., toothpaste) is mixed into 3 grams of deionized water, and then the pH is assessed with a industry accepted pH probe that is calibrated under ambient conditions. The pH is measured by a pH meter with Automatic Temperature Compensating (ATC) probe. The pH meter is capable of reading to 0.001 pH unit.

After each usage the electrode should be washed free from the sample solution with water. Remove any excess water by wiping with a tissue, such as Kimwipes or equivalent. When electrode is not in use, keep electrode tip immersed in pH 7 buffer solution or electrode storage solution. Equipment details are as follows:

pH Meter: Meter capable of reading to 0.01 or 0.001 pH units.
Electrode: Orion Ross Sure-Flow combination: Glass body—VWR #34104-834/Orion #8172BN or VWR#10010-772/Orion #8172BNWP.
Epoxy body—VWR #34104-830/Orion #8165BN or VWR#10010-770/Orion #8165BNWP.
Semi-micro, epoxy body—VWR #34104-837/Orion #8175BN or VWR#10010-774/Orion #3175BNWP.
Orion PerpHect combination: VWR #34104-843/Orion #8203BN semi-micro, glass body.
ATC Probe: Fisher Scientific, Cat. #13-620-16.

pH Buffering Agent

The oral care compositions herein may include an effective amount of a buffering agent or pH trimming agents, as used herein, refer to agents that can be used to adjust the pH of the oral care compositions to the above-identified pH range. The buffering agents include alkali metal hydroxides, ammonium hydroxide, organic ammonium compounds, carbonates, sesquicarbonates, borates, silicates, phosphates, imidazole, and mixtures thereof.

Specific buffering agents include monosodium phosphate (monobasic sodium phosphate), trisodium phosphate (sodium phosphate tribasic dodecahydrate or TSP), sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, sodium citrate, phosphoric acid.

In one embodiment, 0.01% to 3%, preferably from 0.1% to 1% of TSP by weight of the composition, and 0.001% to 2%, preferably from 0.01% to 0.3% of monosodium phosphate by weight of the composition is used. Without wishing to be bound by theory, TSP and monosodium phosphate may have calcium ion chelating activity and therefore provide some monofluorophosphate stabilization (in those formulations containing monofluorophosphate).

Water

The term "orally acceptable carrier" as used herein means a liquid or semi-solid vehicle such as a paste or a gel for containing the active ingredients of the present invention and delivering them to the oral cavity. Water is commonly used as a carrier material in oral compositions due to its many benefits. For example, water is useful as a processing aid, is benign to the oral cavity and assists in quick foaming of toothpastes. Water may be added as an ingredient in its own right or it may be present as a carrier in other common raw materials such as, for example, sorbitol and sodium lauryl sulphate. The term total water content as used herein means the total amount of water present in the oral care composition, whether added separately or as a solvent or carrier for other raw materials but excluding that which may be present as water of crystallization in certain inorganic salts.

The oral care compositions of the present invention comprise at least about 30% of a total water content. In an embodiment, the oral care composition comprises from about 30% to 75% of a total water content. In another embodiment, the oral care composition comprises from about 40% to about 70% of a total water content. In other embodiments, the compositions include from about 45% to about 65%, alternatively from about 40% to about 60%, alternatively from about 50% to about 70%, alternatively from about 50% to about 60%, alternatively from about 45% to about 55%, alternatively from about 55% to about 65%, alternatively from about 50% to about 60%, alternatively about 55%, alternatively combinations thereof, of a total water content. Preferably, the water is USP water.

Chelants

The oral care compositions of the present invention comprise one or more chelants, also known as chelating agents. The term "chelant", as used herein means a bi- or multidentate ligand having at least two groups capable of binding to stannous ions and preferably other divalent or polyvalent metal ions and which, at least as part of a chelant mixture, is capable of solubilising the stannous ions and other optional metal ions within the oral care composition. Groups capable of binding to stannous and other metal ions include carboxyl, hydroxyl and amine groups. Typically, those chelants useful herein will also form water soluble stable complexes with the stannous ions.

Suitable chelants herein include $C_2$-$C_6$ dicarboxylic and tricarboxylic acids, such as succinic acid, malic acid, tartaric acid and citric acid; $C_3$-$C_6$ monocarboxylic acids substituted with hydroxyl, such as gluconic acid; picolinic acid; amino acids such as glycine; salts thereof and mixtures thereof. The chelants can also be a polymer or copolymer in which the chelating ligands are on the same or adjacent monomer.

The oral care composition comprises from 20 mMol to 200 mMol of a chelant. Preferred chelant polymers are polyacids selected from the group consisting of a homopolymer of a monomer, a co-polymer of two or more different monomers, and a combination thereof wherein the monomer or at least one of the two or more different monomers is selected from the group consisting of acrylic acid, methacrylic acid, itaconic acid, maleic acid, glutaconic acid, aconitic acid, citraconic acid, mesaconic acid, fumaric acid and tiglic acid.

Particularly preferred is a methylvinylether/maleic acid (PVM/MA) copolymer. Also suitable are tripolyphosphates. Longer chain linear polyphosphates, though good chelants, are susceptible to hydrolysis in aqueous compositions. Upon hydrolysis they form Olihophosphates which form insoluble zinc complexes. In one embodiment the composition comprises less than 0.1% of polyphosphates having a chain length of four or more.

Preferred organic acid chelants herein comprise citrate, malate, tatirate, gluconate, succinate, lactate, malonate, maleate, and mixtures thereof, whether added in their free acid or salt forms.

Preferred chelants include phytic acid, phytic acid salt (e.g., sodium phytate, potassium phytate), gluconate, and citrate.

Anti-Microbial Agent

The oral care composition comprises from 0.01% to 5%, or from 0.1% to 1% of an anti-microbial agent, preferably an inorganic anti-microbial agent such as a zinc ion source. Preferred zinc ion sources are zinc citrate, zinc gluconate, zinc lactate, and mixtures thereof.

Fluoride Ion Source

The oral care composition may further comprise an effective amount of an anti-caries agent. In one embodiment, the anti-caries agent is a fluoride ion source. In an embodiment, the fluoride ion source may comprise one or a mixture of sodium fluoride, indium fluoride, amine fluoride or sodium monofluorophosphate (MFP). In another embodiment, the fluoride ion source is substantially free of a stannous fluoride. The fluoride ion source may be present in an amount sufficient to give a fluoride ion concentration in the composition at 25° C., and/or in one embodiment can be used at levels of from 0.0025% to 5% by weight of the oral care composition, alternatively from 0.005% to 2.0% by weight of the oral care composition, to provide anti-caries effectiveness. Examples of suitable fluoride ion-yielding materials are disclosed in U.S. Pat. Nos. 3,535,421, and 3,678,154.

In one embodiment, the fluoride ion source is sodium monofluorophosphate, and wherein the composition comprises 0.0025% to 2% of the sodium monofluorophosphate by weight of the composition, alternatively from 0.5% to 1.5%, alternatively from 0.6% to 1.7%, alternatively combinations thereof. In another embodiment, the composition comprises from 0.0025% to 2% of a fluoride ion source by weight of the composition.

Abrasives

Dental abrasives are useful in oral care compositions for their ability to remove surface stains and pellicle and for polishing the teeth. The oral care compositions of the present invention may contain a dental abrasive. Dental abrasives useful in the oral care composition of the subject invention include many different materials. The material selected must be one which is compatible with the composition of interest and does not excessively abrade dentin. Suitable abrasives include, for example, silicas including gels and precipitates, fused silica, insoluble sodium polymetaphosphate, hydrated alumina, and resinous abrasive materials such as particulate condensation products of urea and formaldehyde.

Silica dental abrasives of various types are preferred herein because of their unique benefits of exceptional dental cleaning and polishing performance without unduly abrading tooth enamel or dentine. Silica abrasive polishing materials herein, as well as other abrasives, generally have an average particle size ranging from 0.1 to 30 µm, and preferably from 5 to 15 µm. The abrasive can be precipitated silica or silica gels such as the silica xerogels marketed under the trade name "Syloid" by the W.R. Grace & Company, Davison Chemical Division and precipitated silica materials such as those marketed by the J.M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in more detail in U.S. Pat. Nos. 4,340,583; 5,603,920; 5,589,160; 5,658,553; 5,651,958; and 6,740,311.

Alternatively, mixtures of dental abrasives can be used, such as mixtures of the various grades of Zeodent® silica abrasives as listed above, or mixtures of the silica abrasives and calcium-containing abrasives. Dental solution, mouth spray, mouth wash, and non-abrasive gel compositions of the subject invention typically contain little or no abrasive.

Sweetener

The oral care compositions herein may include a sweetening agent (which is different from a flavorant). These include sweeteners such as saccharin, dextrose, sucrose, lactose, xylitol, maltose, levulose, aspartame, sodium cyclamate, D-tryptophan, dihydrochalcones, acesulfame, sucralose, neotame, and mixtures thereof. Sweetening agents are generally used in oral care compositions at levels of from 0.005% to 5%, alternatively 0.01% to 1%, by weight of the composition, alternatively from 0.1% to 0.5%, alternatively combinations thereof.

Anti-Calculus Agent

The oral care compositions may include an effective amount of an anti-calculus agent, which in one embodiment may be present from 0.05% to 50%, alternatively from 0.75% to 25%, alternatively from 0.1% to 15%. Non-limiting examples include those described in U.S. Publication No. 2011/0104081A1 at paragraph 64, and those described in U.S. Publication No. 2012/0014883A1 at paragraphs 63 to 68, as well as the references cited therein. One example is a pyrophosphate salt as a source of pyrophosphate ion. In one embodiment, the composition comprises tetrasodium pyrophosphate (TSPP) or disodium pyrophosphate or combinations thereof, preferably 0.01% to 2%, more preferably from 0.1% to 1% of the pyrophosphate salt by weight of the composition. Without wishing to be bound by theory, TSPP may provide not only calcium chelating thereby mitigating plaque formation, but also may also provide the additional benefit of monofluorophosphate stabilization (in those formulations containing monofluorophosphate).

Surfactant

The compositions herein may include a surfactant. The surfactant may be selected from anionic, nonionic, amphoteric, zwitterionic, cationic, betaine surfactants, or mixtures thereof. The oral care composition may include a surfactant at a level of from about 0.1% to about 50%, from about 0.025% to about 9%, from about 0.05% to about 5%, from about 0.1% to about 2.5%, from about 0.5% to about 2%, or from about 0.1% to about 1% by weight of the total composition. Non-limiting examples of anionic surfactants may include those described at US 2012/0082630 A1 at paragraphs 32, 33, 34, and 35. Non-limiting examples of zwitterionic or amphoteric surfactants may include those described at US 2012/0082630 A1 at paragraph 36; cationic surfactants may include those described at paragraphs 37 of the reference; and nonionic surfactants may include those described at paragraph 38 of the reference. Preferred surfactant is sodium lauryl sulfate (SLS).

Coloring Agents

The oral care compositions herein may include a coloring agent (i.e., pigments, dyes and opacifiers). The coloring agent may be in the form of an aqueous solution, preferably 1% coloring agent in a solution of water. Titanium dioxide may also be added to the present oral care composition. Titanium dioxide is a white powder which adds opacity to the oral care compositions. Titanium dioxide generally comprises from about 0.25% to about 5%, by weight of the composition. It will be appreciated that selected components for the compositions must be chemically and physically compatible with one another.

Other Ingredients

The present oral care composition can comprise the usual and conventional ancillary components that are known to one skilled in the art. It will be appreciated that selected components for the oral care compositions must be chemically and physically compatible with one another.

Method of Use

The present invention also relates to methods for treating the oral cavity comprising administering to the oral care cavity an oral care composition according to the present invention. In an embodiment, the term "treating" refers to cleaning and polishing teeth. The method of use herein comprises contacting a subject's dental enamel surfaces and oral mucosa with the oral care compositions according to the present invention. The method of treatment may be by brushing with a dentifrice or rinsing with a dentifrice slurry or mouth rinse. Other methods include contacting the topical oral gel, mouthspray, toothpaste, dentifrice, tooth gel, tooth powders, tablets, subgingival gel, foam, mouse, chewing gum, lipstick, sponge, floss, petrolatum gel, or denture product or other form with the subject's teeth and oral mucosa. Depending on the embodiment, the oral care composition may be used as frequently as toothpaste, or may be used less often, for example, weekly, or used by a professional in the form of a prophy paste or other intensive treatment.

EXAMPLES

The following examples and descriptions further clarify embodiments within the scope of the present invention. These examples are given solely for the purpose of illustration and are not to be construed as limitations of the present invention as many variations thereof are possible without departing from the spirit and scope.

Example 1

Toothpaste compositions according to the present invention ("Present Invention Sample 1") and a comparative formulation ("Comparative Sample 1") are shown below with amounts of components in wt %. These compositions are made using conventional methods.

TABLE 1

Oral Care Formulations

| | Amount (Wt %) | |
|---|---|---|
| Ingredients | Present Invention Sample 1 | Comparative Sample 1 |
| Sorbitol | 40.500 | 40.500 |
| Sodium Carboxymethyl Cellulose | 1.300 | 1.300 |
| Carrageenan | 0.700 | 0.700 |
| Hydroxyethyl Cellulose | 0.300 | 0.300 |
| PEG300 | — | 1.000 |
| Water and minors, e.g., color soln. | q.s. | q.s. |
| Target pH | 6-7 | 6-7 |

Example 2

Phase Stability

In order to determine phase stability over a period time for the oral care composition of the present invention, the oil droplet shape and size are determined using scanning electron microscope (SEM). Toothpaste samples are frozen in liquid ethane to do freeze fracture. Samples are then sputter coated with Pd/Au using EMS575X Peltier cooled Sputter coater. SEM images of the sample are obtained using an SEM Hitachi S-4800. The SEM was operated at 3 kV, 14 mm WD, and 15,000× magnification.

Figure 2A:
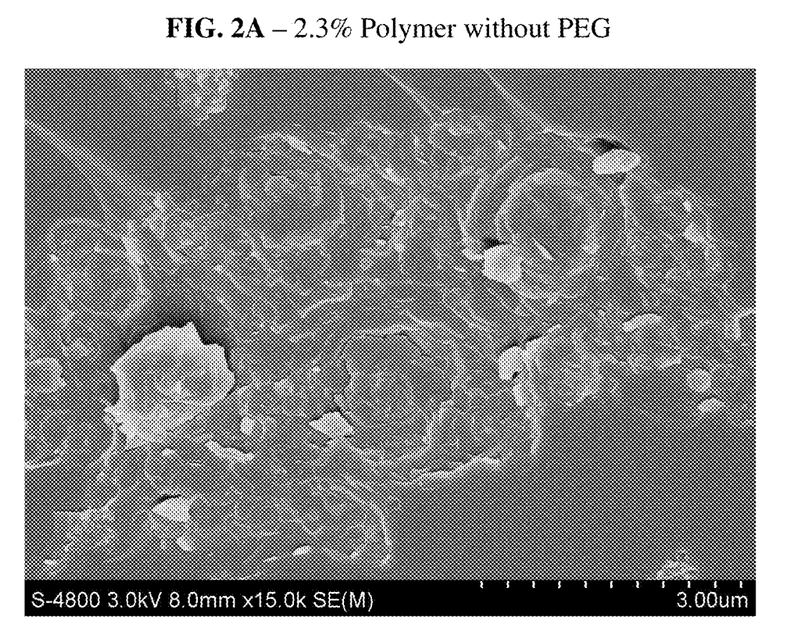
Figure 2B:
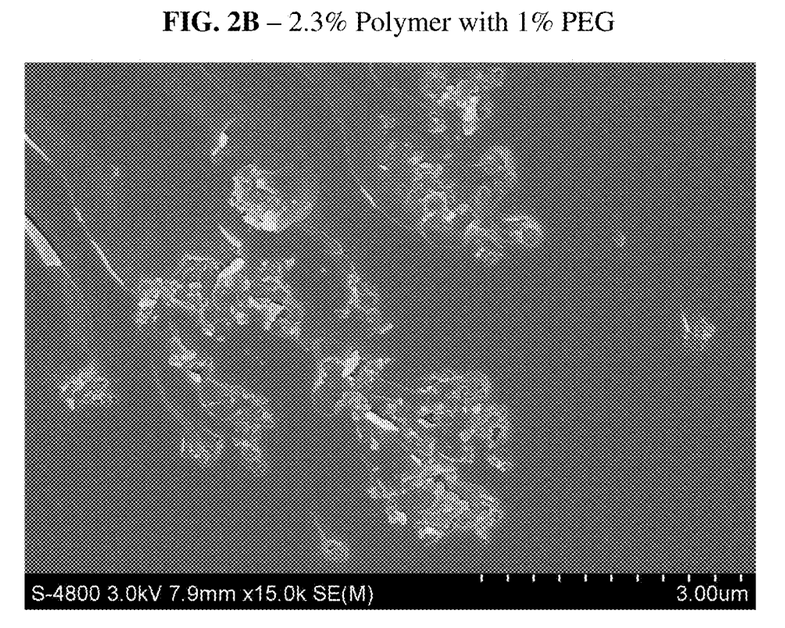

Results:

Micrographs of "Present Invention Sample 1" and "Comparative Sample 1" are shown in FIGS. 2A and 2B, respectively. FIG. 2A shows multi-layered colloidal droplets forming from toothpaste formulated without PEG. FIG. 2B shows no colloidal droplets forming when toothpaste formulated with 1% PEG. By International Union of Pure & Applied Chemistry (IUPAC) the definition a colloid being defined as the dispersed phase particles that have a diameter of between approximately 1 and 1000 nanometers.

Example 3

Toothpaste Formulations

The following examples in Table 2a-2c further describe and demonstrate the use of the present invention within toothpaste embodiments. These examples are given solely for the purpose of illustration and are not to be construed as limitations of the present invention as many variations thereof are possible. Toothpaste compositions are shown below with amounts of components in weight %. These compositions are made using conventional methods.

TABLE 2a

Toothpaste Formulations

| Ingredient | Example A (wt %) | Example B (wt %) | Example C (wt %) | Example D (wt %) |
|---|---|---|---|---|
| Sorbitol sol. (70%) | 40.500 | 40.500 | 40.500 | 40.500 |
| Zinc Citrate | 0.788 | 0.788 | 0.788 | 0.788 |
| Sodium Fluoride | 0.243 | 0.243 | 0.243 | 0.243 |
| Na Carboxymethyl Cellulose (CMC) | 1.300 | 1.300 | 1.150 | 1.150 |
| PEG 300 | — | 1.000 | 1.000 | 3.000 |
| Carrageenan | 0.700 | 0.700 | 0.600 | 0.600 |
| Hydroxyethyl Cellulose (HEC) | 0.300 | 0.300 | 0.300 | 0.300 |
| Silica | 20.000 | 20.000 | 17.000 | 23.000 |
| Sodium Lauryl Sulfate (28% soln.) | 7.500 | 7.500 | 7.000 | 7.000 |
| Sodium Saccharin | 0.580 | 0.580 | 0.580 | 0.580 |
| Flavor | 1.000 | 1.000 | 1.200 | 1.200 |
| Sodium Citrate | 0.274 | 0.274 | 0.274 | 0.274 |
| Water and minors (e.g. color soln.) | q.s | q.s | q.s. | q.s. |
| Target pH | 6-7 | 6-7 | 6-7 | 6-7 |

TABLE 2b

Toothpaste Formulations

| Ingredient | Example E (wt %) | Example F (wt %) | Example G (wt %) | Example H (wt %) |
|---|---|---|---|---|
| Sorbitol sol. (70%) | 40.500 | 40.500 | 55.000 | 55.000 |
| Zinc Citrate | 0.788 | 0.788 | 0.788 | 0.788 |
| Sodium Fluoride | 0.243 | 0.243 | 0.243 | 0.243 |
| Sodium Carboxymethyl Cellulose | 1.150 | 1.150 | 1.150 | 1.150 |
| PEG 300 | — | — | 1.000 | 3.000 |
| PEG 600 | 1.000 | 3.000 | — | — |
| Carrageenan | 0.600 | 0.600 | 0.600 | 0.600 |
| Hydroxyethyl Cellulose | 0.300 | 0.300 | 0.300 | 0.300 |
| Silica | 17.000 | 23.000 | 17.000 | 23.000 |
| Sodium Lauryl Sulfate (28% soln.) | 7.000 | 7.000 | 7.000 | 5.000 |
| Sodium Saccharin | 0.580 | 0.580 | 0.580 | 0.580 |
| Flavor | 1.000 | 1.000 | 1.000 | 1.000 |
| Sodium Citrate | 0.274 | 0.274 | 0.274 | 0.274 |
| Water and minors (e.g. color soln.) | q.s. | q.s. | q.s. | q.s. |
| Target pH | 6-7 | 6-7 | 6-7 | 6-7 |

TABLE 2c

Toothpaste Formulations

| Ingredient | Example I (wt %) | Example J (wt %) | Example K (wt %) | Example L (wt %) |
|---|---|---|---|---|
| Sorbitol sol. (70%) | 55.000 | 55.000 | 40.500 | 40.50 |
| Zinc Citrate | 0.788 | 0.788 | 2.000 | 1.500 |
| Sodium Fluoride | 0.243 | 0.243 | 0.243 | 0.321 |
| Sodium Carboxymethyl Cellulose | 1.150 | 1.150 | 1.150 | 1.150 |
| PEG 300 | — | — | 1.000 | 3.000 |
| PEG 600 | 1.000 | 3.000 | — | — |
| Carrageenan | 0.600 | 0.600 | 0.600 | 0.600 |
| Hydroxyethyl Cellulose | 0.300 | 0.300 | 0.300 | 0.300 |
| Silica | 23.000 | 23.000 | 23.000 | 17.000 |
| Sodium Lauryl Sulfate (28% soln.) | 5.000 | 6.000 | 5.000 | 7.500 |
| Sodium Saccharin | 0.580 | 0.580 | 0.580 | 0.580 |
| Flavor | 1.400 | 1.200 | 1.000 | 1.000 |
| Sodium Citrate | 0.274 | 0.274 | 0.274 | 0.274 |
| Water and minors (e.g. color soln.) | q.s. | q.s. | q.s. | q.s. |
| Target pH | 6-7 | 6-7 | 6-7 | 6-7 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   a) from 0.01% to 5% by weight of a zinc ion source;
   b) from 0.01% to 5% by weight of a flavor composition;
   c) from 30% to 75% by weight of a total water content;
   d) from 0.1% to 3% by weight of a first humectant comprising polyethylene glycols (PEGs) having a weight average molecular weight range of from 300 Da to 8,000 Da; and
   e) from 0.01% to 5% by weight of a thickener system comprising a combination of carboxymethyl cellulose (CMC), hydroxyethyl cellulose (HEC), and carrageenan;
   wherein the oral care composition is substantially free of stannous ions.

2. The oral care composition according to claim 1, wherein the PEGs have an average molecular weight range of from 300 Da to 1,000 Da.

3. The oral care composition according to claim 1, wherein the thickener system comprises of:
   (i) from 0.2% to 2.5% by weight of carboxymethyl cellulose (CMC);
   (ii) from 0.1% to 1.0% by weight of hydroxyethyl cellulose (HEC); and
   (iii) from 0.2% to 2.5% by weight of carrageenan.

4. The oral care composition according to claim 1, further comprising from 35% to 60% by weight of at least one secondary humectant selected from the group consisting of sorbitol, glycerin, xylitol, butylenes glycol, propylene glycol, trimethyl glycine, and mixtures thereof.

5. The oral care composition according to claim 4, wherein the secondary humectant comprises from 40% to 55% by weight of sorbitol.

6. The oral care composition according to claim 1, wherein the pH is from 5 to 8.

7. The oral care composition according to claim 1, wherein the oral care composition is an oil-in-water emulsion having a dispersed phase comprising oil droplets having an average mean particle size of from 1 nm to 100 nm.

8. The oral care composition according to claim 1, wherein the oral care composition is an oil-in-water emulsion having a dispersed phase comprising oil droplets having an average mean particle size of less than 100 nm after 14 days at 40° C.

9. The oral care composition according to claim 1, wherein the oral care composition is visibly phase stable after at least 12 months at ambient conditions.

10. The oral care composition according to claim 1, wherein the zinc ion source is selected from the group consisting of zinc citrate, zinc gluconate, zinc lactate and mixtures thereof.

11. The oral care composition according to claim 1, further comprising from 250 ppm to 5000 ppm of fluoride ions, from a source comprising one or a mixture of sodium fluoride, indium fluoride, amine fluoride or sodium monofluorophosphate (MFP).

12. The oral care composition according to claim 1, wherein the flavor composition has a Dielectric Constant (DEC) from 1 to 15.

13. The oral care composition according to claim 1, wherein the flavor composition has a Water Number (WN) from 1 to 50.

14. The oral care composition according to claim 1, wherein the flavor composition comprises at least 10% by weight of the flavor composition of one or more flavor components having a C log P of less than 2.77.

15. An oral care composition comprising:
   a) from 0.1% to 2% by weight of zinc citrate;
   b) from 0.5% to 2% by weight of a flavor composition;
   c) from 30% to 75% by weight of a total water content;
   d) from 0.1% to 3% by weight of polyethylene glycols (PEGs) having a weight average molecular weight range of from 300 Da to 600 Da; and
   e) from 1% to 2.5% by weight of a thickener system comprising a combination of carboxymethyl cellulose (CMC), hydroxyethyl cellulose (HEC) and carrageenan;
   wherein the oral care composition is substantially free of stannous chloride.

16. A method for treating the oral cavity comprising administering to the oral cavity an oral care composition according to claim 1.

* * * * *

UNITED STATES PATENT AND TRADEMARK OFFICE
CERTIFICATE OF CORRECTION

PATENT NO. : 9,498,416 B2  
APPLICATION NO. : 14/635196  
DATED : November 22, 2016  
INVENTOR(S) : Yujun Li et al.

Page 1 of 1

It is certified that error appears in the above-identified patent and that said Letters Patent is hereby corrected as shown below:

On the Title Page

Item (54), and in the Specification, Column 1, please delete "Oral Care Compositions Having Improved Rheology" and insert -- Oral Care Compositions Having Improved Stability --.

Signed and Sealed this
Tenth Day of January, 2017

Michelle K. Lee
*Director of the United States Patent and Trademark Office*